United States Patent
Rasch-Menges et al.

(10) Patent No.: US 9,456,782 B2
(45) Date of Patent: Oct. 4, 2016

(54) SYSTEMS FOR WITHDRAWING BODY FLUID AND METHODS FOR CONFIGURING SYSTEMS FOR WITHDRAWING BODY FLUIDS

(75) Inventors: Jürgen Rasch-Menges, Schwetzingen (DE); Günter Schmelzeisen-Redeker, Lorsch (DE); Jochen Schulat, Mannheim (DE); Wilfried Schmid, Mannheim (DE); Rudolf Pachl, Ellerstadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 264 days.

(21) Appl. No.: 13/272,734

(22) Filed: Oct. 13, 2011

(65) Prior Publication Data

US 2012/0035504 A1 Feb. 9, 2012

Related U.S. Application Data

(63) Continuation of application No. 11/332,930, filed on Jan. 17, 2006, now Pat. No. 8,062,274, which is a continuation of application No. PCT/EP2004/007409, filed on Jul. 7, 2004.

(30) Foreign Application Priority Data

Jul. 16, 2003 (DE) .................................. 103 32 283

(51) Int. Cl.
| | |
|---|---|
| *A61B 5/15* | (2006.01) |
| *A61B 5/00* | (2006.01) |
| *A61B 5/151* | (2006.01) |
| *A61B 5/157* | (2006.01) |

(52) U.S. Cl.
CPC ............. *A61B 5/489* (2013.01); *A61B 5/1411* (2013.01); *A61B 5/157* (2013.01);

(Continued)

(58) Field of Classification Search
CPC ........ A61F 13/15; A61F 13/47; A61F 13/49; A61F 13/51; A61F 13/58; A61F 13/60; A61F 13/62; A61B 5/1411; A61B 5/150022; A61B 5/150068; A61B 5/150175; A61B 5/150389; A61B 5/150412; A61B 5/150503; A61B 5/150954; A61B 5/15109; A61B 5/157; A61B 5/441; A61B 5/6843
USPC .................. 604/289, 290, 540; 600/504, 578
See application file for complete search history.

(56) References Cited

U.S. PATENT DOCUMENTS

| | | | |
|---|---|---|---|
| 3,358,689 | A | 12/1967 | Higgins |
| 5,318,584 | A | 6/1994 | Lange et al. |

(Continued)

FOREIGN PATENT DOCUMENTS

| | | |
|---|---|---|
| WO | WO 01/89383 A2 | 11/2001 |
| WO | 2002 100276 A1 | 12/2002 |

(Continued)

*Primary Examiner* — Peter S Vasat
(74) *Attorney, Agent, or Firm* — Woodard Emhardt Moriarty McNett and Henry LLP

(57) ABSTRACT

The invention relates to a system for withdrawing body fluid from a body part via a withdrawal site located on the surface of the body part, with at least one sensor for detecting at least one variable dependent on the location or state of the withdrawal site, and with an evaluation unit for evaluating the at least one variable detected by the at least one sensor and for triggering a reaction, dependent on the value of the detected variable, in the system for withdrawing body fluid, said reaction serving to prepare the system for puncturing the surface of the body part, and with at least one puncturing device for creating an opening in the body at the withdrawal site. The invention further relates to an integrated analysis system, to a method for configuring a system for withdrawal of body fluid, and to a method for selecting a menu item from a menu for controlling a system for withdrawing body fluid from a body part.

9 Claims, 1 Drawing Sheet

(52) U.S. Cl.
CPC .. *A61B 5/150022* (2013.01); *A61B 5/150068* (2013.01); *A61B 5/15109* (2013.01); *A61B 5/15186* (2013.01); *A61B 5/150954* (2013.01); *A61B 5/6843* (2013.01); *A61B 5/150175* (2013.01); *A61B 5/150389* (2013.01); *A61B 5/150412* (2013.01); *A61B 5/150503* (2013.01); *A61B 5/441* (2013.01)

(56) References Cited

U.S. PATENT DOCUMENTS

| | | |
|---|---|---|
| 5,857,983 A | 1/1999 | Douglas et al. |
| 5,857,984 A | 1/1999 | deBoer et al. |
| 5,951,492 A | 9/1999 | Douglas et al. |
| 6,319,210 B1 | 11/2001 | Douglas et al. |
| 6,589,260 B1 * | 7/2003 | Schmelzeisen-Redeker et al. .............. 606/181 |
| 2003/0060716 A1 | 3/2003 | Heidrich |
| 2003/0069509 A1 * | 4/2003 | Matzinger et al. ........... 600/504 |

FOREIGN PATENT DOCUMENTS

| | | |
|---|---|---|
| WO | WO 02/100251 A2 | 12/2002 |
| WO | WO 02/100254 A2 | 12/2002 |
| WO | WO 02/100276 A1 | 12/2002 |
| WO | WO 02/101343 A2 | 12/2002 |

* cited by examiner

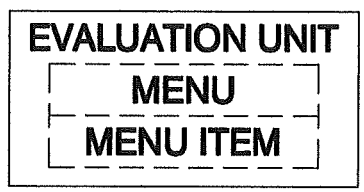
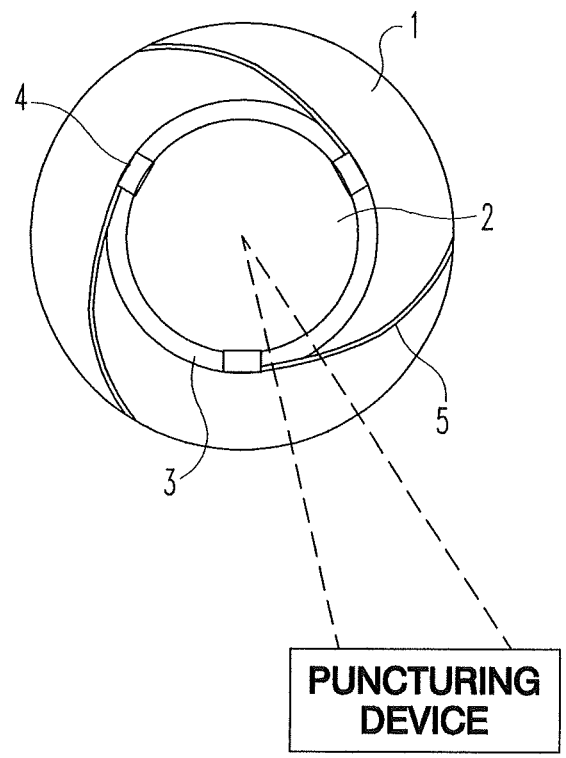

SYSTEMS FOR WITHDRAWING BODY FLUID AND METHODS FOR CONFIGURING SYSTEMS FOR WITHDRAWING BODY FLUIDS

REFERENCE TO RELATED APPLICATIONS

The present application is a continuation of application Ser. No. 11/332,930, filed Jan. 17, 2006, now U.S. Pat. No. 8,062,274 which is a continuation of PCT Patent Application No. PCT/EP2004/007409, filed Jul. 7, 2004, which claims priority to German Patent Application No. 103 32 283.3, filed Jul. 16, 2003, all of which are hereby incorporated by reference in their entirety.

TECHNICAL FIELD

The present invention relates to a system for withdrawing body fluid from a body part, to an integrated analysis system for analyzing the body fluid, and to a method for configuring a withdrawal device which is used to withdraw body fluid from a body part.

BACKGROUND

Body fluids are mainly withdrawn for the purpose of subsequent analysis, in order to permit diagnosis of diseases or to monitor a patient's metabolism. This kind of withdrawal is carried out on diabetics in particular, in order to determine the blood sugar concentration.

In the prior art, blood sampling systems have for some time been known with which the patient or hospital staff can withdraw fluid in a simple manner. An example of an appliance suitable for this purpose is the commercially available Softclix lancing device, whose operation is described in U.S. Pat. No. Re. 35,803. This appliance provides a possibility of setting the depth of insertion of a lancet into the tissue. Thus, the patient is able to select the minimum depth of insertion with which he obtains just the right amount of blood for subsequent analysis, and he can thus minimize the pain caused by puncturing the skin. After the patient has created an opening in the skin by puncturing it, then, particularly in the case of shallow insertion depths, he has to rub or apply pressure to the finger in order to extract sufficient blood from the puncture wound.

A further system for withdrawing body fluid is known from U.S. Pat. No. 5,857,983. This system comprises a hollow puncturing element for creating an incision at the withdrawal site, and a collection tube which communicates with the puncturing element. A so-called stimulator incites flow of body fluid from the puncture by compressing a ring of body tissue around the puncture. During this process, the puncturing element is moved within the incision by means of a movement mechanism in order to keep the incision open during withdrawal of the body fluid. A suction mechanism sucks the body fluid through the puncturing element into the collection tube. In this appliance too, it is possible to set the depth of insertion of the puncturing element.

U.S. Pat. No. 5,951,492 relates to a further system for withdrawing body fluid. It comprises a mechanism for creating a puncture in the skin of the user, and a sample-withdrawing element in order to convey the body fluid through the puncture and via a capillary element onto a test strip, which receives the body fluid from the capillary element. This system also comprises a sample-identifying mechanism which detects a droplet of body fluid on the surface of the user's skin.

U.S. Pat. No. 6,319,210 relates to another system for withdrawing body fluid, in particular blood or interstitial fluid. This document describes a puncturing mechanism which is also intended to be suitable for withdrawal sites other than the finger pad. Here once again, a stimulator is used to incite the body fluid to flow from an incision, the stimulator either being heated or vibrated.

PCT Patent Publication No. WO 01/89383 discloses a system for withdrawing body fluid from an area of a body part, in particular the finger pad, with a compression unit onto which the body part is pressed in a primary direction and which converts the pressure partially into a movement in a secondary direction, partially transverse to the primary direction, so that the internal pressure in an area of the body part is increased. This system further comprises a puncturing device, in particular a lancet or cannula, for creating an opening in the body in the area of increased internal pressure, the compression unit having a press-on area made of a deformable material.

However, the systems from the prior art are not able to detect the withdrawal conditions, in particular the location of the withdrawal and the state of the skin at the withdrawal site, nor are they able to adjust automatically to these withdrawal conditions in order to ensure that body fluid can be withdrawn as painlessly as possible and in as short a time as possible, with the fewest possible maneuvers by the user.

Different withdrawal sites (for example finger pad or forearm) require different parameter sets for withdrawal of the body fluid and also for its analysis. The volume of blood attainable from the forearm is very much smaller. Furthermore, the puncture needed is much deeper compared to when collecting a sample from the finger. At the same time, there is less need for precise control of the puncture depth, because the overall sensitivity to pain is lower and is influenced less by the puncture depth. If the parameter set for withdrawal of blood from the forearm was applied for withdrawing blood from the finger pad, this would involve an extremely deep and thus very painful incision. Further disadvantages are of a hygienic nature, because incorrect use of the forearm puncture parameters leads to far too great a sample volume, as a result of which the system may be soiled.

Moreover, the parameter sets ought to be adapted to the state of the skin at the withdrawal site, for example to the skin temperature. Generally, the warmer the skin, the better its blood circulation, and the easier it is to collect blood from it.

For substantially pain-free withdrawal of body fluid, it is also important that this is done only when the withdrawal site is lying correctly on the withdrawal system, that is to say with sufficient pressure and over a sufficiently large surface area.

It is therefore an object of the present invention to make available a system and a method for withdrawing body fluid, which system and method avoid the aforementioned disadvantages of the prior art and permit substantially painless withdrawal of body fluid in a short space of time and with the fewest possible maneuvers by the user. They are also intended to permit withdrawal of body fluid at different withdrawal sites (alternate site testing) and with different states of the withdrawal site, the system being intended to automatically adjust to the withdrawal conditions.

SUMMARY

According to the present invention, a system is provided for withdrawing body fluid from a body part via a withdrawal site located on the surface of the body part, with at least one sensor for detecting at least one variable dependent on the location or state of the withdrawal site, and with an evaluation unit for evaluating the at least one variable detected by the at least one sensor and for triggering a reaction, dependent on the value of the detected variable, in the system for withdrawing body fluid, said reaction serving to prepare the system for puncturing the surface of the body part, and with at least one puncturing device for creating an opening in the body at the withdrawal site.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawing in which:

FIG. 1 is a diagrammatic representation of a press-on area in a system for withdrawing body fluid, with sensors contained therein.

Skilled artisans appreciate that elements in the figures are illustrated for simplicity and clarity and have not necessarily been drawn to scale. For example, the dimensions of some of the elements in the FIGURE may be exaggerated relative to other elements to help improve understanding of the embodiment(s) of the present invention.

In order that the invention may be more readily understood, reference is made to the following examples, which are intended to illustrate the invention, but not limit the scope thereof.

DETAILED DESCRIPTION

The following description of the preferred embodiment is merely exemplary in nature and is in no way intended to limit the invention or its application or uses.

FIG. 1 shows a cone-shaped press-on area 1 with a circular opening 2 arranged at the center. During withdrawal of the body fluid, the press-on area 1 is pressed onto the corresponding body part via a ring-shaped part 3 surrounding the opening 2 and arranged on the top face of the cone-shaped press-on area 1. A puncturing device is guided through the opening 2 (perpendicular to the plane of the drawing) towards the body surface. In the preferred embodiment of the present invention illustrated in FIG. 1, the ring-shaped part 3 comprises sensors 4 which lie on the body surface during the withdrawal procedure and concentrically surround the withdrawal site. These are sensors for detecting at least one variable dependent on the location and state of the withdrawal site, and can be used in the system according to the invention for withdrawing body fluid, or for measurement in the method according to the invention for configuring such a system. For example, the sensors 4 can be electrodes which can be used for measuring the temperature, the electrical resistance, the electrical conductivity, the electrical current strength or the electrical voltage. The sensors are connected to electrical leads, glass fibers or similar 5. These can be arranged in a spiral formation in the cone-shaped press-on area 1 so that they can effectively take up the pressure loads repeatedly arising during the withdrawal procedure. To produce such a press-on area 1 with sensors 4, the sensors 4 can, for example, be fitted in a molding tool and encapsulated by an in-flowing plastic. On the surfaces via which the sensors are fitted in the molding tool, they remain free of plastic and are consequently freely accessible to the user on the top face of the ring-shaped part 3 of the press-on area 1. The preferred material of the sensors is dependent on the application. A PT 100 sensor, for example, can be used for measuring the temperature.

The system for withdrawing body fluid can be used simply to create an opening in the body through which the body fluid can flow. However, it can also comprise other mechanisms which serve to collect the body fluid, in particular mechanisms for inciting the body fluid to flow out of the body opening and mechanisms for applying the body fluid onto a test element, on which it is subsequently analyzed. In general, analysis systems designed for the private user operate with disposable test elements which, after coming into contact with a sample of fluid, emit a signal as a function of the analyte concentration. In the field of blood sugar measurement, optical test elements can be used, in which the reaction of glucose with a test chemical leads to a color change. Electrochemical test elements can also be used, in which an enzymatic conversion of glucose permits amperometric or potentiometric analysis. The test elements can advantageously be designed so that they take up body fluid actively (for example via a capillary opening).

According to the invention, the system for withdrawing body fluid comprises at least one sensor. The latter detects at least one variable dependent on the location and state of the withdrawal site. The withdrawal site is the location on the surface of the body part at which the body fluid, upon withdrawal, flows through an opening in the body. An evaluation unit evaluates the detected variable. For example, it calculates other variables dependent on this variable and relevant to the necessary withdrawal parameters. It then triggers a reaction, dependent on the value of the detected variable, in the system for withdrawing body fluid, in particular the selection and use of a defined parameter set for carrying out the withdrawal of body fluid, the system preferably having a large number of user-specific parameter sets, from which one is assigned to the value measured with the sensor. The aim of the triggered reaction is to ensure that the system for withdrawing body fluid has a configuration that is optimized for the withdrawal of body fluid. It prepares the system for optimal puncturing of the surface of the body part before the puncturing device is activated. In the prior art, the use of sensors in blood-sampling devices is known, for example from PCT Patent Publication Nos. WO 02/101343 A2, WO 02/100251 A2 and WO 02/100254 A2. However, these sensors are not used to prepare the device for the puncturing and withdrawal procedure to be performed, and instead they detect various parameters during the sampling procedure and automatically trigger the puncturing.

According to the invention, at least one puncturing device serves to create an opening in the body at the withdrawal site. Such a puncturing device can be a lancet or cannula, as are known in the prior art. Lancets usually have a metal needle, one end of which is ground to a point. The rear part of the lancet needle remote from the tip is usually enclosed by a lancet body made of plastic. Such lancets are known for example from U.S. Pat. No. 3,358,689.

In the case of a lancet, the latter is preferably removed completely from the tissue after the puncture, so that the puncture site from which the body fluid flows is accessible. In the case of a cannula, the latter can remain at the maximum depth of insertion, in order to convey body fluid from this depth, or alternatively it can be drawn back as far as the surface of the skin in order to collect fluid from there. It is also possible to draw the cannula back only partially, so that the puncture channel is partially freed but the cannula remains in the skin. In this way, on the one hand, the fluid is better able to flow out of the exposed puncture channel, and, on the other hand, it is not necessary to position the cannula on the body surface.

The sensor included in the system according to the invention for withdrawal of body fluid is preferably a sensor for detecting at least one of the variables of temperature, electrical resistance, electrical conductivity, electrical current strength, electrical voltage, position, inclination, pressure, acceleration, and optical variables.

For temperature measurement, the temperature dependency of electrical resistance materials with positive or negative temperature coefficients is used, for example, the temperature sensor being designed as a contact thermometer. However, a sensor is also conceivable which measures, without contact, the infrared radiation emanating from the body part in the area of the withdrawal site. For example, the measurement site is imaged onto a radiation-sensitive element which thus warms up in relation to its surroundings. This small temperature difference can be measured by thermo-elements.

A sensor for measuring electrical resistance and a sensor for measuring electrical conductivity comprises, for example, electrodes connected to a Wheatstone bridge.

Sensors for measuring electrical current strength or electrical voltage can contain electrodes connected to an ammeter or to a voltmeter.

Sensors for detecting position or inclination can, for example, be mercury switches.

The pressure measurement by means of pressure sensors is effected directly, via membrane deformation, or by a force sensor. Known types of pressure sensors are, for example, thick-film or semiconductor pressure sensors or piezoelectric sensors.

Acceleration sensors known in the prior art are, inter alia, Hall acceleration sensors containing a Hall-effect sensor, piezoelectric sensors, or capacitive silicon acceleration sensors.

Sensors for detecting optical variables encompass sensors designed for any type of optical variable, including fiber-optic sensors for different variables, for example for measuring reflected electromagnetic radiation.

In a preferred embodiment of the present invention, the sensor is a temperature sensor for detecting the skin temperature on the surface of the body part at the withdrawal site. An important parameter for successful blood sampling is skin temperature. Generally, the warmer the skin, the better the blood circulation, and the easier it is to collect blood. Conversely, blood sampling is very difficult at very low skin temperatures. This means that it is expedient to check the temperature near the withdrawal site, for example so that the appliance emits a warning if the skin is too cold. Moreover, withdrawal parameters such as puncture depth and duration of the withdrawal procedure can be adapted to the actual skin temperature. The temperature sensor for detecting the skin temperature should be able to detect the temperature as close as possible to the withdrawal site.

In a further embodiment of the present invention, the sensor is a sensor for detecting the electrical resistance or the electrical conductivity of the skin on the surface of the body part at the withdrawal site. By detecting the skin resistance or conductivity, it is possible, for example, to determine whether there is sufficient contact between the body part, from which the body fluid is to be withdrawn, and the system for withdrawing body fluid, or whether, for example, the user has moved his finger away between the puncturing procedure and the blood-sampling procedure. It is also conceivable that, by measuring the skin resistance or conductivity, the system for withdrawing body fluid can determine whether the user is using the appliance on the finger or on other body parts and can select the appropriate parameters.

In a further preferred embodiment of the present invention, the sensor is a position or inclination sensor for detecting the position or inclination of the system upon contact with the withdrawal site. The sensor for detecting the position or inclination can be used to automatically identify the manner in which the user is holding the appliance and, from this, can deduce the intended withdrawal site (for example finger pad, earlobe or forearm). In the case of withdrawal of body fluid from the forearm, the measurement system must be able to cope with extremely small sample volumes. In this case, a preferred orientation of the appliance is one in which the sample is collected in the direction of the force of gravity (ABA—Automatic Blood Application) since in this way the best yield can be achieved. In the case of withdrawal from the finger pad in the direction of the force of gravity, there is a risk of soiling the appliance with too large a sample volume. Consequently, in the case of withdrawal of body fluid from the finger pad, the preferred orientation of the appliance is counter to the force of gravity. Therefore, from the position or inclination of the appliance, it is possible to draw conclusions concerning the intended withdrawal site.

In a further embodiment of the present invention, the sensor is a pressure sensor for detecting the pressure with which a press-on area of the system is applied to the surface of the body part at the withdrawal site. To "express" the body fluid out of the opening made in the body by means of the puncturing device, many systems in the prior art (for example PCT Patent Publication No. WO 01/89383) comprise a compression unit with which the internal pressure in the area of the withdrawal site is increased. The user presses the body part at the withdrawal site onto the optionally deformable compression unit. He leaves the body part in this pressed-on state during formation of a skin opening and optionally also during collection of the body fluid. A pressure sensor can check whether the pressure with which the area of skin is pressed onto the compression unit is sufficient to collect the body fluid, and, if appropriate, it can determine the required duration of withdrawal or take other measures to ensure collection of a sufficient sample volume. If the system for withdrawal of body fluid is used exclusively to create an opening in the skin with the aid of the puncturing device, the pressure sensor can check whether the user is pressing a body part onto a press-on area of the appliance and is thus indicating his readiness to activate the puncturing device. However, in contrast to the pressure sensor disclosed in PCT Patent Publication No. WO 02/100254, the pressure sensor according to the invention is not used to automatically trigger the puncturing, but only to prepare or adapt the system for optimal puncturing of the surface of the body part.

In a further embodiment of the present invention, the sensor is an inductive, optical or capacitive proximity sensor for detecting the distance of the withdrawal site, located on the surface of the body part, from a press-on area of the system. The press-on area of the system is that area with which the system is pressed onto the surface of the body part during withdrawal of body fluid, e.g., a compression unit as mentioned above. The proximity sensor is intended to detect whether the body part is situated on the press-on area or at a distance from it, and, as a result, to either release or block the puncturing device.

The evaluation unit of the system according to the invention for withdrawing body fluid preferably evaluates the variable detected by the respective sensor and then triggers one of the following reactions depending on the value of the detected variable:

blocking or releasing of the at least one puncturing device, setting the puncture depth of the puncturing device selected for creating the opening in the body, setting the geometric shape of a press-on area of the system for withdrawing body fluid, setting the cross section of an opening in a press-on area of the system for withdrawing body fluid, through which opening the puncturing device can penetrate into the surface of the body part, selecting one of at least two press-on areas included in the system for withdrawing body fluid, selecting one of at least two puncturing devices contained in the system for withdrawing body fluid, setting the duration of the withdrawal procedure, displaying text on a display device, and displaying or setting evaluation parameters which are used by a device for analyzing the body fluid.

Releasing or blocking of the puncturing device is expedient, for example, when the variable measured by a pressure sensor, proximity sensor, resistance sensor or conductivity sensor indicates that the withdrawal site of a body part is located or not located in a position suitable for puncturing, for example pressed with sufficient or insufficient pressure onto a compression unit. In the case of release of the puncturing device, the system is ready for activation of the puncturing device. The puncturing can then be triggered, preferably manually by the user. Blocking of the puncturing device can also take place if a skin temperature sensor detects that the skin temperature is below a defined temperature where the blood circulation in the skin is expected to be inadequate for collecting blood.

The puncture depth of the puncturing device selected for creating the opening in the body can be set on the basis of the variables detected by one of the abovementioned sensors. The puncture depth selected is as shallow as possible in order to substantially avoid pain and scarring of the user. The settings preferably range between puncture depths of 0.5 and 2 mm. If, for example, the variable detected with a temperature sensor, position sensor, inclination sensor, resistance sensor or conductivity sensor indicates a puncture site (for example finger, arm, earlobe), the puncture depth can be set so that it is adapted to the conditions at this withdrawal site and so that the desired volume of fluid is thus collected. This therefore permits automatic blood sampling at a plurality of sampling sites.

The geometric shape of a press-on area of the system for withdrawing body fluid can also be set. In this case, the geometric shape is adapted to the conditions of the withdrawal site. The cross section of an opening in the press-on area of the system for withdrawing body fluid is preferably set, through which opening the puncturing device can penetrate into the surface of the body part. For example, in the case of a cone-shaped press-on area in which the puncturing device is guided through a circular opening onto the body surface, the diameter of the circular opening varies. With a suitable choice of diameter, the cone-shaped press-on area fits snugly onto the body part, in particular the finger pad or forearm, during withdrawal of the body fluid. The variations in the diameter of the opening can, for example, follow the principle of an iris diaphragm. A further possible setting of the geometric shape of the press-on area involves adjusting the distance between two parallel rods acting as a support for the body part.

A further possible reaction of the system for withdrawing body fluid is the selection of one of at least two press-on areas if, from the at least one variable detected by the at least one sensor, a conclusion is drawn regarding the withdrawal location. For example, the system can trigger an automatic displacement of the different press-on areas on a slide, by which means a selected press-on area adapted to the withdrawal site is driven into a position in which the system for withdrawing body fluid is ready to use the selected press-on area.

The selection of one of at least two puncturing devices contained in the system for withdrawing body fluid is also possible. Thus, it is possible to select and use the puncturing device ideally suited for the selected withdrawal site (for example finger, arm) and for the state of the latter (for example temperature).

A further possible reaction of the system according to the invention for withdrawing body fluid is the setting of the duration of the withdrawal procedure, if the system is used not just for puncturing, but also for collecting blood, for example by pressing blood out of the body opening or collecting it via a cannula. The duration of the withdrawal procedure is the time during which the user is intended to leave the body part applied to the system, in particular to a press-on area, so as to collect a sufficient volume of body fluid. The optimal duration for collecting the volume of body fluid ideal for analysis is, for example, dependent on the skin temperature, on the withdrawal location, in particular the thickness of the skin there, and on the puncture depth.

Moreover, a text can be displayed on a display device of the system on the basis of the at least one variable detected by the at least one sensor. This text can, for example, contain a warning which warns the user against continuing with the withdrawal procedure if the conditions for withdrawal of body fluid are unfavorable or unsuitable, for example if the skin at the withdrawal site is too cold, or if the body part does not lie uniformly or with sufficient pressure on the press-on area, or if the system for withdrawing body fluid has an operating error. It is also conceivable to display a user menu, for example if, on the basis of the variable detected with a sensor, no clear conclusion can be drawn concerning the location or state of the withdrawal site, so that the user is requested to input the required information into the system.

Moreover, on the basis of the detected variable, it is possible to display or to set evaluation parameters which are used by a device for analyzing body fluid. Thus, for example, the different composition of the body fluid withdrawn at different withdrawal sites (for example finger pad or forearm) can be taken into account in the analysis.

In a preferred embodiment of the present invention, the system for withdrawing body fluid comprises a compression unit for increasing the internal pressure in the area of the withdrawal site when collecting the body fluid. This is, for example, a compression unit as is known from PCT Patent Publication No. WO 01/89383 A2. By using this compression unit, the so-called milking movement for expressing blood from the puncture site can be imitated in a way which is simple and convenient for the user. Not only does the compression unit deliver larger quantities of body fluid than is the case with other press-on devices of the prior art; the press-on and withdrawal procedure is also much more convenient for the patient. This is due, firstly, to the fact that the compression unit fits snugly on the body part, in particular a finger. In addition, however, there is also the fact that the compression unit allows sufficient quantities of body fluid to be collected even with very shallow puncture depths. Another very important advantage of the invention is that, by using a compression unit with a press-on area made of deformable material, it is possible to withdraw body fluid reliably and conveniently from differently shaped body parts. In particular, therefore, body fluid can be withdrawn easily and reliably from fingers of different sizes. In addition, by means of the deformable material, it is possible to compensate for shape differences of the pressed-on body part (tip of the finger versus side of the finger). In this way, capillary blood can be collected particularly advantageously from the finger pad. In addition, it is also possible to withdraw blood or interstitial fluid from other body parts, for example the arm. The compression unit has the effect that the compression of the body part not only takes place in the direction of the primary contact pressure, but that the contact pressure is also at least partly converted in such a way that a compression takes place with force components transverse to the primary contact pressure. The area of the body part at which fluid is to be withdrawn is in this way laterally compressed. By means of the compression unit, the internal pressure in an area of the body part is increased. This area of increased internal pressure is adjacent to the area on which the pressure acts, and it is surrounded by a press-on area. A puncturing device can puncture the skin at the area of increased internal pressure, and body fluid can be withdrawn from here. The compression unit includes a press-on area made of a deformable material. Such a material on the one hand makes the withdrawal procedure more convenient for the user, and on the other hand it also makes for easier adaptation to differently shaped or differently sized body parts. Examples of materials for the press-on area are deformable plastics such as elastomers, rubber and the like. However, other compression units are also conceivable which, in the system according to the invention for withdrawing body fluid, increase the internal pressure in the area of the withdrawal site when collecting the body fluid.

In the system according to the invention for withdrawing body fluid, at least one sensor is preferably arranged in the press-on area of the system. The press-on area is in this case adjacent to the withdrawal site or surrounds the latter, so that the variable detected with the sensor is detected as close as possible to the withdrawal site, in order to permit as precise as possible a conclusion concerning the location and state of the withdrawal site.

The invention further relates to an integrated analysis system comprising a system according to the invention for withdrawing body fluid from a body part, and a device for analyzing at least one property of the body fluid. It is advantageous for there to be a high degree of automation if the integrated analysis system is used both for puncturing the withdrawal site and also for collecting and analyzing the body fluid. The integrated analysis system advantageously requires only a small number of maneuvers on the part of the user. For example, the user only presses on the compression unit in the press-on area, and all the subsequent steps including output of the analysis result can proceed automatically. Devices for analyzing at least one property of the body fluid are known in the prior art. Examples of devices which are commercially available are the blood glucose analysis systems sold under the name ACCU-CHEK® Compact Plus and ACCU-CHEK® Advantage from Roche Diagnostics Corporation, Indianapolis, Ind.

The system according to the invention for withdrawing body fluid is preferably used for withdrawing blood or interstitial fluid, preferably from the finger pad or from the forearm. The integrated analysis system according to the invention is preferably used for withdrawing blood or interstitial fluid and for analyzing the glucose content in the blood or in the interstitial fluid.

Another subject of the present invention is a method for configuring a system for withdrawing body fluid, which system is used for withdrawing body fluid from a body part via a withdrawal site, said method comprising the steps of measuring at least one variable dependent on the location and state of the withdrawal site, and selecting a setting, which is dependent on the value of the measured variable and influences the withdrawal of body fluid, in the system for withdrawing body fluid.

By measuring the at least one variable dependent on the location and state of the withdrawal site, and by the resulting selection of the setting which influences the withdrawal of the body fluid, the system for withdrawing body fluid can be automatically and optimally adapted to the withdrawal conditions (for example skin temperature, shape of the body part, thickness of the skin, contact pressure of the body part) before the skin is punctured.

In the method according to the invention, at least one of the following variables is preferably measured: temperature, electrical resistance, electrical conductivity, electrical current strength, electrical voltage, position, inclination, pressure, acceleration, and optical variables.

In the method according to the invention, at least one of the following settings is preferably selected as a function of the value of the measured variable:

blocking or releasing of a puncturing device, setting a puncture depth of a puncturing device selected for generating the opening in the body, setting a geometric shape of a press-on area of the system for withdrawing body fluid, setting the cross section of an opening in a press-on area of the system for withdrawing body fluid, through which opening a puncturing device can penetrate into the surface of the body part, selecting one of at least two press-on areas included in the system for withdrawing body fluid, selecting one of at least two puncturing devices contained in the system for withdrawing body fluid, setting the duration of the withdrawal procedure, displaying text on a display device, and displaying or setting evaluation parameters which are used by a system for analyzing body fluid.

As regards the measured variables and the settings as a function of the value of the measured variable, the statements made above in relation to the system according to the invention for withdrawing body fluid likewise apply to the method according to the invention.

It is also conceivable for the value of the measured variable to be stored on a storage medium using GPS and/or radio-clock information. Thus, for example, a measured value can be stored together with position coordinates and clock time, so that this information can be called up at a later time and can be used, for example, for statistical evaluation.

Referring again to FIG. 1, another subject of the present invention is a method for selecting a menu item from a menu for controlling a system for withdrawing body fluid from a body part, said method comprising the steps of measuring one of the variables of temperature, electrical resistance, electrical conductivity, electrical current strength, electrical voltage, position, inclination, pressure, acceleration, or optical variables, and selecting the menu item as a function of the value of the measured variable.

In this way, the user, without pressing a key, is able to make a selection from the menu for controlling the system for withdrawing body fluid by means of a sensorily detectable influence of one of these variables. For measuring the evaluated variable, a sensor used in the measurement in step A) of the method according to the invention can likewise be used to configure a system for withdrawing body fluid. In the method according to the invention for selecting a menu item from a menu for controlling a system for withdrawing body fluid, the inclination, position or acceleration, for example, can be measured with the aid of an inclination sensor, position sensor or acceleration sensor. The user can select the inclination or position, and can accelerate the system for withdrawing body fluid in a defined direction, in such a way that he gives the measured variable a defined value which in turn is assigned to a defined menu item in the menu. In this way, the user can quickly and conveniently make a selection from the menu. This makes it possible, for example, to create integrated analysis systems of high efficiency.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for configuring a system for withdrawing body fluid from a body part via a withdrawal site, comprising:
    measuring a value of at least one variable dependent on the location and state of the withdrawal site by using a sensor, wherein at least one of the following variables is measured: temperature, electrical resistance, electrical conductivity, electrical current strength, electrical voltage, position, inclination, pressure, acceleration, or optical variables;
    selecting a setting, which is dependent on the value of the measured variable to thereby influence the withdrawal of body fluid, in the system wherein the setting is selected dependent on the value of the measured at least one variable and by the selection of the setting the system for withdrawing body fluid is automatically adapted to withdrawal conditions before skin at the withdrawal site is punctured;
    wherein at least one of the following settings is selected as a function of the value of the measured variable:
    blocking or releasing of a puncturing device, wherein the releasing of the puncturing device is bringing the puncturing device into a state ready for activation;
    setting a puncture depth of a puncturing device selected for creating an opening in the body;
    setting a geometric shape of a press-on area of the system;
    setting the cross section of an opening in a press-on area of the system through which opening a puncturing device can penetrate into a surface of the body part;
    selecting one of at least two press-on areas included in the system;
    selecting one of at least two puncturing devices contained in the system;
    setting a duration of a body fluid withdrawal procedure;
    displaying text on a display device; or
    displaying or setting evaluation parameters which are used by the system for analyzing body fluid; and
    wherein the value of the measured variable is stored on a storage medium using GPS or radio-clock information.

2. The method of claim 1, wherein the sensor comprises at least one of the following sensors: a pressure sensor, a proximity sensor, a resistance sensor, or a conductivity sensor, wherein the setting comprises a blocking or releasing of a puncturing value of the variable detected by the pressure sensor, the proximity sensor, the resistance sensor or the conductivity sensor indicates that the withdrawal site of the body part is pressed with sufficient or insufficient pressure onto a compression unit.

3. The method of claim 1 wherein the withdrawal conditions are selected from the group consisting of skin temperature, shape of the body part, thickness of the skin and contact pressure of the body part.

4. The method of claim 1, wherein the system comprises a compression unit for increasing an internal pressure in the area of the withdrawal site when collecting the body fluid, in such a way that body fluid is expressed out of the opening, wherein said compression unit converts pressure exerted in a primary direction into a movement into a secondary direction so that the internal pressure in an area of the body part is increased.

5. A method for selecting a menu item from a menu in a system for controlling a system for withdrawing body fluid from a body part, comprising:
    measuring a value of one or more variables including temperature, electrical resistance, electrical conductivity, electrical current strength, electrical voltage, position, inclination, pressure, acceleration, or optical variables, the variables corresponding to the location and state of the withdrawal site; and
    selecting the menu item from the menu as a function of the value of the measured variable, wherein the menu item may be at least one of:
        blocking or releasing of a puncturing device, wherein the releasing of the puncturing device is bringing the puncturing device into a state ready for activation;
        setting a puncture depth of a puncturing device selected for creating an opening in the body;
        setting a geometric shape of a press-on area of the system;
        setting the cross section of an opening in a press-on area of the system through which opening a puncturing device can penetrate into a surface of the body part;

selecting one of at least two press-on areas included in the system;

selecting one of at least two puncturing devices contained in the system;

setting a duration of a body fluid withdrawal procedure;

displaying text on a display device; or displaying or setting evaluation parameters which are used by the system for analyzing body fluid.

6. The method of claim 5 wherein the value of the measured variable is stored on a storage medium using GPS or radio-clock information.

7. A method for configuring a system for withdrawing body fluid from a body part via a withdrawal site, comprising:

measuring a value of at least one variable dependent on the location and state of the withdrawal site by using a sensor, wherein at least one of the following variables is measured: temperature, electrical resistance, electrical conductivity, electrical current strength, electrical voltage, position, inclination, pressure, acceleration, or optical variables;

selecting a setting, which is dependent on the value of the measured variable to thereby influence the withdrawal of body fluid, in the system wherein the setting is selected dependent on the value of the measured at least one variable and by the selection of the setting the system for withdrawing body fluid is automatically adapted to withdrawal conditions before skin at the withdrawal site is punctured;

wherein at least one of the following settings is selected as a function of the value of the measured variable:

blocking or releasing of a puncturing device, wherein the releasing of the puncturing device is bringing the puncturing device into a state ready for activation;

setting a puncture depth of a puncturing device selected for creating an opening in the body;

setting a geometric shape of a press-on area of the system;

setting the cross section of an opening in a press-on area of the system through which opening a puncturing device can penetrate into a surface of the body part;

selecting one of at least two press-on areas included in the system;

selecting one of at least two puncturing devices contained in the system;

setting a duration of a body fluid withdrawal procedure;

displaying text on a display device; or displaying or setting evaluation parameters which are used by the system for analyzing body fluid; and wherein the system comprises a compression unit for increasing an internal pressure in the area of the withdrawal site when collecting the body fluid, in such a way that body fluid is expressed out of the opening, wherein said compression unit converts pressure exerted in a primary direction into a movement into a secondary direction so that the internal pressure in an area of the body part is increased.

8. The method of claim 7, wherein the sensor comprises at least one of the following sensors: a pressure sensor, a proximity sensor, a resistance sensor, or a conductivity sensor, wherein the setting comprises a blocking or releasing of a puncturing device when the variable detected by the pressure sensor, the proximity sensor, the resistance sensor or the conductivity sensor indicates that the withdrawal site of the body part is pressed with sufficient or insufficient pressure onto a compression unit.

9. The method of claim 7, wherein the withdrawal conditions are selected from the group consisting of skin temperature, shape of the body part, thickness of the skin and contact pressure of the body part.

* * * * *